United States Patent [19]

Truog

[11] Patent Number: 4,620,973

[45] Date of Patent: Nov. 4, 1986

[54] USE OF NOOTROPICS

[75] Inventor: Peter Truog, Bottmingen, Switzerland

[73] Assignee: Ciba-Geigy Corporation, Ardsley, N.Y.

[21] Appl. No.: 745,335

[22] Filed: Jun. 14, 1985

Related U.S. Application Data

[63] Continuation of Ser. No. 418,147, Sep. 15, 1982, abandoned, which is a continuation of Ser. No. 232,343, Feb. 6, 1981, abandoned.

[30] Foreign Application Priority Data

Feb. 13, 1980 [CH] Switzerland .......................... 1169/80

[51] Int. Cl.⁴ ............................................. A61K 31/40

[52] U.S. Cl. ..................................... 424/10; 514/424; 514/425

[58] Field of Search ................... 424/10; 514/424, 425

[56] References Cited

PUBLICATIONS

Chemical Abstracts 92: 15506t, (1-30-80).

Primary Examiner—Jerome D. Goldberg
Attorney, Agent, or Firm—Joseph G. Kolodny

[57] ABSTRACT

The invention relates to the use of nootropics, particularly Piracetam ®, in connection with the treatment of cancer with cytostatically effective preparations, for the prevention or mitigation of side effects which are caused by cytostatics.

4 Claims, No Drawings

USE OF NOOTROPICS

This is a continuation of application Ser. No. 418,147, filed 9/15/82 (now abandoned) which is a continuation of Ser. No. 232,343 filed 2/6/81 (now abandoned).

The present invention relates to the use of nootropics, particularly Piracetam ®, for the prevention or alleviation of side effects which can occur in connection with the treatment of tumour diseases by the use of cytostatically effective compounds.

The treatment of cancer diseases by the use of cytostatically effective chemotherapeutica is becoming more and more extensive, both as a treatment on its own or together with other types of treatment, such as the surgical removal of tumour tissues and/or radiotherapy. New active substances having an increased and/or more specific effectiveness along with better compatibility are being continuously tested and introduced. It is however known that, in spite of the increased therapeutic range most cytostatically effective compounds give rise to a series of more or less grave side effects which are common to virtually all these preparations. Apart from the various side effects which in part are specific to certain preparations, such as myocardiotoxic effects, the occurring side effects on cells having a high rate of division, such as those of bone marrow, the gastro-intestinal tract and hair, are particularly strongly marked and frequent. The last mentioned effects in the treatment with cytostatics very often cause nausea, vomiting, diarrhea and loss of hair.

It has now been established that side effects can be surprisingly prevented or at least mitigated by the administration of so-called nootropics in combination with the treatment using cytostatics on relatively rapidly proliferating cellular tissues. The side effects concerned are in particular nausea and vomiting, as well as loss of hair, and so forth.

The present invention relates therefore to the use of nootropics in combination with the treatment of cancer by means of cytostatically effective preparations.

The present invention relates especially to the use of nootropics, in combination with the treatment of cancer by means of cytostatically effective prepartions, for the prevention or mitigation of toxic side effects which are caused by cytostatics.

The present invention relates above all to the use of nootropics, in combination with the treatment of cancer with cytostatically effective preparations, for the prevention or mitigation of side effects which are attributable to the influencing as a result of cytostatics or relatively rapidly proliferating cellular tissues.

By nootropics are meant in the first place compounds which have an action on the central nervous system, and which have a direct positive effect on higher psychic and mental functions, such as learning capacity and memory. The pharmacological action profile of nootropics, which is responsive for the ascertained clinical effects, is at present only partially understood.

In connection with the present invention, it has been shown that nootropics which can be advantageously used according to the invention are in particular those of the type of the formula

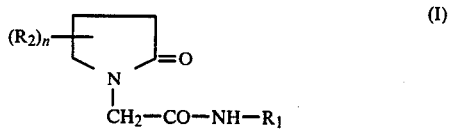

wherein $R_1$ is hydrogen or the radical of the formula

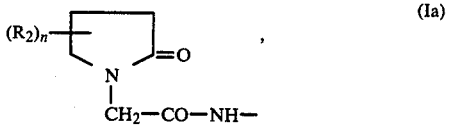

$R_2$ is lower alkyl, especially methyl and n is an integer from 0 to 4, particularly however 0 or 1, or if $R_1$ is hydrogen and n is 1 $R_2$ has the meaning of hydroxy whereby compounds of these types wherein n is other than zero can occur in the form of isomeric mixtures, for example racemates, or in the form of pure isomers, for example optically active antipodes. Particularly suitable compounds in this respect are those of the formula I wherein $R_1$ is hydrogen and n is 0 (Piracetam ®), or a radical of the formula Ia, and wherein $R_2$ is methyl which occupies in the 2-oxo-1-pyrrolidinyl radical the 5-position, and n is zero (Dupracetam ®,), or 1, where in the latter case the compound can occur in the fom of an isomeric mixture or as a pure isomer, or those compounds of formula I, wherein $R_1$ is hydrogen, n is 1 and $R_2$ has the meaning of hydroxy, which occupies in the 2-oxo-1-pyrrolidinyl radical the 4-position. The compound in particular used according to the invention is Piracetam ®.

In addition to using nootropically effective compounds of the above type, it is possible according to the invention to also use nootropics of the vincamine type, for example Vincamin ®, or a pharmaceutically applicable acid addition salt thereof, as well as other nootropically effective compounds.

The nootropically effective compounds used according to the invention can be applied in the form of pharmaceutical preparations able to be administered enterally or parenterally (intravenously or by means of infusion). The doses administered are those cusxomarily used to obtain nootropical effects, for example from about 0.1 g to about 5 g of a compound of the type of the formula I per single dose, whereby the dose can vary greatly depending on the form of administration.

It has also been shown that the customarily occurring side effects attributable to the cytostatically effective preparation can be most effectively prevented, or the consequences thereof best mitigated, by administration of the nootropically effective preparation in particular before the treatment with one or more cytostatically effective preparations, that is to say, by a prophylatic administration of the nootropic. The nootropically effective preparation is usually administered a relatively short time, i.e. about 15 to 60 minutes, before the treatment with the cytostatic, whereby the parenteral, especially intravenous, administration about 30 minutes before the treatment with the cytostatic(s) is preferred.

In connection with the present invention, it is possible to administer, in the form of cytostatically effective preparations, the most varied compounds having such effects and the stated side effects, particularly the toxic side effects associated with rapidly proliferating cellular tissues, such as nausea and vomiting, loss of hair, and so forth; the cytostatics are administered in the doses and the intervals recommended for the appropriate cancer treatment, very often also in combination. Reference is made in this connection to Brunner and Nagel, Internistische Krebstherapie (second edition, 1979, Springer Verlag, Berlin, Heidelberg, N.Y.)

It can be shown by means of animal experiments that the toxic side effects which can occur in connection with the treatment of tumour diseases with cytostatics are favourably influenced as a result of the administration of nootropics. When for example mice are treated with a single application (10.0 or 12.5 mg/kg i.p.) of adriamycin as the cytostatic in the presence or absence of Piracetam, it is shown that Piracetam significantly reduces the mortality rate of the mice treated with adriamycin. The computer analysis of the data obtained verifies that Piracetam has therefore clearly increased the probability of survival ($p<0.01$).

The use of nootropically effective compounds in the treatment of tumour diseases with cytostatically effective preparations can be illustrated on the basis of clinical tests. It can be demonstrated that with the application of Piracetam in connection with the treatment with cytostatically effective preparations of a total number of 47 patients, there was no occurrence of alopecia in 32 of the patients. The cardioprotective action of Pyracetam against the side effects of adriamycin, which has previously been shown in animal tests, can be verified clinically, since patients who have received more than 550 mg/ of adriamycin have so far suffered no clinically identifiable cardiac damage, for example cardiac insufficiency.

Clinical Test Procedure 2000 mg of Piracetam (preparation: Nootropil ®) are administered intraveneously to a patient suffering from a tumour disease, for example a female patient with breast cancer. The treatment is commenced after 30 minutes with one or more cytostatics, for example adriamycin (preparation: Adriblastin ®), vincristine (preparation: Oncovin ®), and/or cyclophosphamide (preparation: Endoxan ®), the dosage of these preparations being adjusted according to the condition of the tumour disease and being customarily administered intravenously. The same treatment, that is, administration of Piracetam, followed by the cytostatic(s), is repeated depending on the course of the disease.

EXAMPLE 1

To a patient suffering from a mamma-carcinoma there were administered intravenously 2000 mg of Piracetam 30 minutes before the intravenous administration to the patient of 110 mg of adriamycin and 1400 mg of cyclophosphamide (Endoxan). There was no occurrence of alopecia even after a prolonged period of treatment.

EXAMPLE 2

To a patient suffering from NH lymphoma (stage IV) there were administered intravenously 2000 mg of Piracetam 30 minutes before the chemotherapeutic intravenous administration to the patient of 150 mg of adriamycin, 16.0 mg of vincristine and 4800 mg of cyclophosphamide (Endoxan), or alternatively the peroral administration of 24,250 mg of cyclophosphamide (Endoxan). There was no occurrence of alopecia even after a prolonged period of treatment.

EXAMPLE 3

To a patient suffering from a mamma-carcinoma there were administered intravenously 2000 mg of Piracetam 30 minutes before the chemotherapeutic intravenous administration to the patient of 100 mg of adriamycin, 3.8 mg of vincristine, 900 mg of cyclophosphamide (Endoxan), 280 mg of methotrexate and 7900 mg of 5-fluoro-uracil. Throughout a prolonged period of treatment, that is, after repeated therapy, there was no occurrence of alopecia.

EXAMPLE 4

To a patient suffering from a lung carcinoma there were administered intravenously 2000 mg of Piracetam 30 minutes before the chemotherapeutic intravenous administration to the patient of 180 mg of adriamycin, 5.4 mg of vincristine, 3200 mg of cyclophosphamide (Endoxan) and 500 mg of veperide (podophyllotoxin derivative). With a prolonged treatment, that is, with repeated therapy, there was no occurrence of alopecia.

EXAMPLE 5

To a patient suffering from a mamma-carcinoma there were administered intravenously 2000 mg of Piracetam 30 minutes before the intravenous administration to the patient of 1275 mg of adriamycin and peroral administration of 30,000 mg of cyclophosphamide (Endoxan). With a prolonged treatment, that is, with repeated therapy, there was no occurrence of alopecia, and also no sign of cardiac insufficiency.

EXAMPLE 6

To a patient suffering from a sigma carcinoma there were administered intravenously 2000 mg of Piracetam 30 minutes before the intravenous administration to the patient of 140 mg of adriamycin, 400 mg of cyclophosphamide (Endoxan) and 38,500 mg of 5-fluoro-uracil. There was no occurrence of alopecia even after a prolonged treatment.

EXAMPLE 7

To a patient suffering from smoldering leukaemia there were administered intravenously 2000 mg of Piracetam 30 minutes before the intravenous administration to the patient of 8.4 mg of vincristine and 1100 mg of cyclophosphamide (Endoxan). No alopecia occurred throughout a prolonged period of treatment.

Cytostatics, in connection with treatment therewith the nootropics according to the invention are administered, are, inter alia, alkylating substances, such as mechlorethamine [nitrogen mustard or N,N-bis-(2-chloroethyl)-N-methyl-amine], triethylenephosphoramide [tri-(1-aziridinyl)-phosphine oxide], cyclophosphamide [2-[bis-(2-chlorethyl)-amino]-3,4,5,6-tetrahydro-2H-1,3,2-oxazophosphorine-2-oxide], ifosfamide [2-(2-chloroethyl)-amino-3-(2-chloroethyl)-3,4,5,6-tetrahydro-2H-1,3,2-oxazophosphorine-2-oxide], chlorambucil [4-{4[-di-(2-chloroethyl)-amino]-phenyl}-butyric acid], busulfan [1,4-di-(methanesulfonyloxy)-butane], melphalan [p-di-(2-chloroethyl)-amino-2-phenylalanine]-or triaziquone [2,3,5-tri-(1-(1-aziridinyl)-p-benzoquinone], also nitrosourea compounds, such as carmustine [N,N'-di-(2-chloroethyl)-N-nitrosourea], or CCNU [N-(2-chloroethyl)-N'-cyclohexyl-N-nitrosourea]. Also used are antimetabolites, such as methotrexate (amethopterine or L-(+)-N-[4-N-(2,4-diamino-6-pteridinyl)-methyl-N-methyl-amino]-benzoyl-glutamic acid), mercaptopurine

[6-mercapto-7H-purine], thioguanine [2-amino-6-mercapto-7H-purine], cytarabine [cytosine-arabinoside or 1-β-D-arabinofuranosyl-cytosine], fluoruracil [5-fluoro-1H,3H-pyrimidine-2,4-dione], floxuridine [5-fluorodeoxyuridine or 1-(2-deoxy-β-D-ribofuranosyl)-5-fluoruracil], or ftorafur [1-(2-tetrahydrofuryl)-5-fluoruracil]. A further group of cytostatics include vinblastine [vincaleukoblastine] and vincristine [leurocristine], as well as certain antibiotics, such as actinomycin-D, daunorubicin, doxorubicin [adriamycin], mithramycin [aureolic acid], streptonigrin, mitomycins and bleomycins. Further suitable cytostatics are, inter alia, procarbacine [4-(2-methylhydrazino)-methyl-benzoic acid-isopropylamide], hydroxyurea, [N-hydroxy-urea], L-asparaginase, dacarbazine (DTIC or 5-(3,3-dimethyl-1-triazenyl)-1H-imidazole-4-carboxamide], mitotane [o,p'-DDD or 2,2-dichloro-1-(4-chlorophenyl)-1-(2-chlorophenyl)-ethane], estramustine [3-0-(N,N-di-(2-chloroethyl)carbamoyl)-ostradiol], or podophyllotoxin. The above-mentioned cytostatically effective compounds having salt-forming properties can optionally be used also in the form of their pharmazeutically applicable salts.

As in the case of the nootropically effective compounds, the cytostatically acting compounds are used in the form of pharmaceutically applicable preparations for oral or preferably parenteral, such as intravenous administration or in a form suitable for infusion. The preparation forms already described above can also be used in connection with the cytostatically effective compounds.

What is claimed is:

1. A method for mitigating the side effects of cytostatics agents wherein said side effects are selected from the group consisting of myocardiotoxic effects and side effects on bone marrow cells, gastro-intestinal cells and hair cells which comprises administering an effective amount of nootropics of formula I

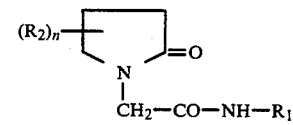

wherein
$R_1$ is hydrogen and $R_2$ is hydroxy and n is an integer from 0 to 1, whereby compounds of the formula I wherein n is 1 can occur in the form of isomeric mixtures or in the form of pure isomers, for mitigating side-effects to a patient undergoing cytostatics treatment for cancer.

2. A method according to claim 1, characterized in that cyclophosphamide or adriamycin is combined with piracetam.

3. A method according to claim 1, characterized in that cyclophosphamide or adriamycin is combined with 4-hydroxypiracetam.

4. Method according to claim 3 wherein cyclophosphamide is combined with 4-hydroxypiracetam.

* * * * *